United States Patent
Joshi et al.

(10) Patent No.: US 9,089,712 B2
(45) Date of Patent: Jul. 28, 2015

(54) IMPLANTABLE MEDICAL DEVICE WITHOUT ANTENNA FEEDTHROUGH

(75) Inventors: Himanshu Joshi, Houston, TX (US); Darrell N. Fuller, Friendswood, TX (US)

(73) Assignee: CYBERONICS, INC., Houston, TX (US)

( * ) Notice: Subject to any disclaimer, the term of this patent is extended or adjusted under 35 U.S.C. 154(b) by 252 days.

(21) Appl. No.: 13/558,640

(22) Filed: Jul. 26, 2012

(65) Prior Publication Data

US 2012/0287004 A1 Nov. 15, 2012

Related U.S. Application Data

(63) Continuation-in-part of application No. 13/328,241, filed on Dec. 16, 2011, which is a continuation-in-part of application No. 13/098,276, filed on Apr. 29, 2011, now Pat. No. 8,516,662.

(51) Int. Cl.
| | |
|---|---|
| *H04B 1/38* | (2006.01) |
| *A61N 1/372* | (2006.01) |
| *H01Q 1/27* | (2006.01) |
| *H01Q 7/00* | (2006.01) |
| *H01Q 13/10* | (2006.01) |
| *A61N 1/37* | (2006.01) |
| *A61N 1/375* | (2006.01) |

(52) U.S. Cl.
CPC ............ *A61N 1/37229* (2013.01); *H01Q 1/273* (2013.01); *H01Q 7/00* (2013.01); *H01Q 13/10* (2013.01); *A61N 1/375* (2013.01); *A61N 1/3718* (2013.01); *Y10T 29/49993* (2015.01)

(58) Field of Classification Search
CPC ............ H04B 1/38; A61F 2002/30331; A61F 2002/4475; A61F 2310/00023; A61F 2/3094; A61F 2/4455; A61F 2/82; A61L 2300/00; A61L 2300/416; A61L 2300/426; A61L 2300/604; A61L 2300/802; A61L 31/022; A61L 31/143; A61L 31/16
USPC ............ 607/32, 36, 37, 59, 60, 101, 116, 138
See application file for complete search history.

(56) References Cited

U.S. PATENT DOCUMENTS

| | | |
|---|---|---|
| 4,030,480 A | 6/1977 | Meyer |
| 4,075,632 A | 2/1978 | Baldwin et al. |
| 4,127,110 A | 11/1978 | Bullara |
| 4,305,397 A | 12/1981 | Weisbrod et al. |
| 4,414,979 A | 11/1983 | Hirshorn et al. |
| 4,441,498 A | 4/1984 | Nordling |

(Continued)

OTHER PUBLICATIONS

International Application No. PCT/US2012/032007, International Search Report and Written Opinion of the International Searching Authority dated Sep. 13, 2013, 13 pages.

(Continued)

*Primary Examiner* — Edward Urban
*Assistant Examiner* — Max Mathew
(74) *Attorney, Agent, or Firm* — Cyberonics, Inc.

(57) ABSTRACT

An implantable medical device includes a case having a conductive housing defining an opening. A dielectric material is coupled to the conductive housing to hermetically seal the opening. A header block is coupled to the case over the dielectric material. An antenna is within the case under the dielectric material and there is no antenna feedthrough extending through the case into the header block.

10 Claims, 10 Drawing Sheets

(56) References Cited

U.S. PATENT DOCUMENTS

| | | |
|---|---|---|
| RE32,361 E | 2/1987 | Duggan |
| 4,800,899 A | 1/1989 | Elliott |
| 4,823,812 A | 4/1989 | Eshel et al. |
| 5,035,231 A | 7/1991 | Kubokawa et al. |
| 5,050,605 A | 9/1991 | Eydelman et al. |
| 5,058,581 A | 10/1991 | Silvian |
| 5,109,853 A | 5/1992 | Taicher et al. |
| 5,117,825 A | 6/1992 | Grevious |
| 5,168,871 A | 12/1992 | Grevious |
| 5,246,000 A | 9/1993 | Ellis et al. |
| 5,313,953 A | 5/1994 | Yomtov et al. |
| 5,314,453 A | 5/1994 | Jeutter |
| 5,330,518 A | 7/1994 | Neilson et al. |
| 5,336,245 A | 8/1994 | Adams et al. |
| 5,350,411 A | 9/1994 | Ryan et al. |
| 5,373,852 A | 12/1994 | Harrison et al. |
| 5,375,596 A | 12/1994 | Twiss et al. |
| 5,383,912 A | 1/1995 | Cox et al. |
| 5,402,788 A | 4/1995 | Fujio et al. |
| 5,456,698 A | 10/1995 | Byland et al. |
| 5,494,030 A | 2/1996 | Swartz et al. |
| 5,558,618 A | 9/1996 | Maniglia |
| 5,562,714 A | 10/1996 | Grevious |
| 5,629,678 A | 5/1997 | Gargano et al. |
| 5,630,835 A | 5/1997 | Brownlee |
| 5,697,958 A | 12/1997 | Paul et al. |
| 5,720,770 A | 2/1998 | Nappholz et al. |
| 5,735,887 A | 4/1998 | Barreras, Sr. et al. |
| 5,766,232 A | 6/1998 | Grevious et al. |
| 5,782,891 A | 7/1998 | Hassler et al. |
| 5,788,692 A | 8/1998 | Campbell et al. |
| 5,800,494 A | 9/1998 | Campbell et al. |
| 5,840,148 A | 11/1998 | Campbell et al. |
| 5,861,019 A | 1/1999 | Sun et al. |
| 5,873,840 A | 2/1999 | Neff |
| 5,902,251 A | 5/1999 | vanHooydonk |
| 5,928,145 A | 7/1999 | Ocali et al. |
| 5,951,594 A | 9/1999 | Kerver |
| 5,963,132 A | 10/1999 | Yoakum |
| 5,967,986 A | 10/1999 | Cimochowski et al. |
| 6,009,350 A | 12/1999 | Renken |
| 6,009,878 A | 1/2000 | Weijand et al. |
| 6,041,256 A | 3/2000 | Michel |
| 6,073,050 A | 6/2000 | Griffith |
| 6,115,634 A | 9/2000 | Donders et al. |
| 6,161,049 A | 12/2000 | Rudie et al. |
| 6,167,312 A | 12/2000 | Goedeke |
| 6,169,925 B1 | 1/2001 | Villaseca et al. |
| 6,175,768 B1 | 1/2001 | Arndt et al. |
| 6,176,856 B1 | 1/2001 | Jandak et al. |
| 6,190,382 B1 | 2/2001 | Ormsby et al. |
| 6,192,279 B1 | 2/2001 | Barreras, Sr. et al. |
| 6,201,993 B1 | 3/2001 | Kruse et al. |
| 6,240,317 B1 | 5/2001 | Villaseca et al. |
| 6,261,247 B1 | 7/2001 | Ishikawa et al. |
| 6,275,737 B1 | 8/2001 | Mann |
| 6,277,113 B1 | 8/2001 | Berube |
| 6,308,101 B1 | 10/2001 | Faltys et al. |
| 6,308,102 B1 | 10/2001 | Sieracki et al. |
| 6,379,300 B1 | 4/2002 | Haubrich |
| 6,393,327 B1 | 5/2002 | Scribner |
| 6,398,710 B1 | 6/2002 | Ishikawa et al. |
| 6,456,256 B1 | 9/2002 | Amundson et al. |
| 6,463,329 B1 | 10/2002 | Goedeke |
| 6,477,425 B1 | 11/2002 | Nowick et al. |
| 6,485,462 B1 | 11/2002 | Kriesel |
| 6,505,072 B1 | 1/2003 | Linder et al. |
| 6,516,227 B1 | 2/2003 | Meadows et al. |
| 6,561,975 B1 | 5/2003 | Pool et al. |
| 6,574,510 B2 | 6/2003 | Von Arx et al. |
| 6,610,054 B1 | 8/2003 | Edwards et al. |
| 6,614,406 B2* | 9/2003 | Amundson et al. ............ 343/873 |
| 6,631,290 B1 | 10/2003 | Guck et al. |
| 6,675,810 B2 | 1/2004 | Krag |
| 6,682,480 B1 | 1/2004 | Habib et al. |
| 6,708,065 B2* | 3/2004 | Von Arx et al. ................ 607/60 |
| 6,805,667 B2 | 10/2004 | Christopherson et al. |
| 6,894,616 B1 | 5/2005 | Forster |
| 6,922,591 B2 | 7/2005 | Single |
| 6,924,773 B1 | 8/2005 | Paratte |
| 7,016,733 B2* | 3/2006 | Dublin et al. ................... 607/36 |
| 7,042,357 B2 | 5/2006 | Girvin et al. |
| 7,043,307 B1 | 5/2006 | Zelickson et al. |
| 7,092,763 B1 | 8/2006 | Griffith et al. |
| 7,146,861 B1 | 12/2006 | Cook et al. |
| 7,149,578 B2 | 12/2006 | Edvardsson |
| 7,174,212 B1* | 2/2007 | Klehn et al. .................... 607/36 |
| 7,191,013 B1 | 3/2007 | Miranda et al. |
| 7,203,549 B2 | 4/2007 | Schommer et al. |
| 7,209,792 B1 | 4/2007 | Parramon et al. |
| 7,212,866 B1 | 5/2007 | Griffith |
| 7,235,096 B1 | 6/2007 | Van Tassel et al. |
| 7,281,314 B2 | 10/2007 | Hess et al. |
| 7,286,877 B2 | 10/2007 | Daum |
| 7,317,946 B2* | 1/2008 | Twetan et al. ................... 607/60 |
| 7,399,280 B2 | 7/2008 | Liu et al. |
| 7,429,255 B2 | 9/2008 | Thompson |
| 7,432,723 B2 | 10/2008 | Ellis et al. |
| 7,483,732 B2 | 1/2009 | Zhong et al. |
| 7,483,752 B2 | 1/2009 | Von Arx et al. |
| 7,554,493 B1 | 6/2009 | Rahman |
| 7,561,921 B2 | 7/2009 | Phillips et al. |
| 7,577,476 B2 | 8/2009 | Hochman et al. |
| 7,695,435 B2 | 4/2010 | Benson et al. |
| 7,729,766 B2 | 6/2010 | Toy et al. |
| 7,860,476 B1 | 12/2010 | Karr et al. |
| 7,904,167 B2 | 3/2011 | Klosterman et al. |
| 7,983,760 B2 | 7/2011 | Ginggen et al. |
| 8,332,037 B2* | 12/2012 | Imran .............................. 607/36 |
| 8,442,643 B2 | 5/2013 | Toy et al. |
| 8,725,263 B2* | 5/2014 | Yamamoto et al. ............. 607/37 |
| 8,738,111 B2* | 5/2014 | Sweeney et al. ............. 600/381 |
| 2005/0113886 A1* | 5/2005 | Fischell et al. ................... 607/60 |
| 2005/0222633 A1 | 10/2005 | Edvardsson |
| 2006/0028784 A1 | 2/2006 | Brendel |
| 2006/0247712 A1 | 11/2006 | Fuller et al. |
| 2007/0273606 A1 | 11/2007 | Mak et al. |
| 2008/0033500 A1 | 2/2008 | Strother et al. |
| 2008/0091242 A1* | 4/2008 | Kamath et al. ..................... 607/6 |
| 2009/0228075 A1* | 9/2009 | Dion ................................ 607/60 |
| 2010/0060431 A1 | 3/2010 | Stevenson et al. |
| 2010/0109966 A1* | 5/2010 | Mateychuk et al. .......... 343/841 |
| 2010/0114205 A1 | 5/2010 | Donofrio et al. |
| 2010/2114205 | 5/2010 | Donofrio et al. |
| 2010/0161002 A1 | 6/2010 | Aghassian et al. |
| 2010/0168818 A1 | 7/2010 | Barror et al. |
| 2010/0194541 A1 | 8/2010 | Stevenson et al. |
| 2010/0321163 A1 | 12/2010 | Stevenson |
| 2011/0004076 A1 | 1/2011 | Janna et al. |
| 2012/0071942 A1* | 3/2012 | Kamath et al. .................. 607/14 |
| 2012/0276856 A1 | 11/2012 | Joshi et al. |
| 2013/0289666 A1* | 10/2013 | Johnson et al. ................. 607/63 |

OTHER PUBLICATIONS

International Application No. PCT/US2013/050420, International Search Report and Written Opinion Dated Sep. 17, 2013, 13 pages.

\* cited by examiner

IMPLANTABLE MEDICAL DEVICE WITHOUT ANTENNA FEEDTHROUGH

CROSS-REFERENCE TO RELATED APPLICATIONS

This application is a continuation-in-part of and claims priority to U.S. patent application Ser. No. 13/328,241 filed Dec. 16, 2011 which is a continuation-in-part of and claims priority to U.S. patent application Ser. No. 13/098,279 filed Apr. 29, 2011, both of which are incorporated herein by reference in their entirety.

FIELD OF THE DISCLOSURE

The present disclosure is generally related to implantable medical devices with internal antennas.

SUMMARY

A particular embodiment of the disclosure relates to an implantable medical device which includes a case having a conductive housing defining an opening. A dielectric material is coupled to the conductive housing to hermetically seal the opening. A header block is coupled to the case over the dielectric material. An antenna is within the case under the dielectric material and there is no antenna feedthrough extending through the case into the header block.

Another particular embodiment of the disclosure relates to an implantable medical device which includes a case having a conductive housing defining an opening. A dielectric material is coupled to the conductive housing to hermetically seal the opening. An antenna is within the case under the dielectric material and the antenna is not electrically connected to the case. The case substantially blocking external radio frequency signals from being received by the antenna unless the external radio frequency signals are in line of site of the antenna through the opening in the case Another particular embodiment of the disclosure relates to a method that includes positioning an antenna in a portion of a case of an implantable medical device. The case includes a conductive housing that defines an opening where the antenna is not electrically connected to the conductive housing. The method includes coupling a dielectric material to the conductive housing to hermetically seal the opening. The antenna is positioned under the dielectric material inside the case. The method also includes hermetically sealing the case and coupling a header block to the case over the dielectric material and there is no antenna feedthrough extending through the case into the header block.

BRIEF DESCRIPTION OF THE DRAWINGS

The disclosure will become more fully understood from the following detailed description, taken in conjunction with the accompanying drawings.

DETAILED DESCRIPTION

In the following description, "over," "under," "behind," "beneath" and similar terms are used to denote relative positions of particular components or elements when an implantable medical device (IMD) is in a particular orientation (e.g., a side view orientation depicted in FIG. 3), and such terms do not denote an absolute position of the particular components or elements. For example, as used herein, a first component of the IMD is "over" a second component when the IMD is in the side view orientation depicted in FIG. 3 and the first component is closer to a top surface of the IMD (i.e., a first surface 320 of an IMD 100 in FIG. 3) than the second component. Obviously, the IMD could be turned over such that positions of the first surface 320 and a second surface 322 of FIG. 3 were reversed without changing the physical arrangement of the first and second components. As the term is used herein, the first component would still be "over" the second components despite reversing or otherwise changing the orientation of the IMD 100 since the terms are defined relative to the particular orientation of the IMD 100 illustrated in FIG. 3. Thus, for consistency and for ease of description, relative positions of the components of IMDs are defined and described herein with reference to the orientation illustrated in FIG. 3.

Figure 1:
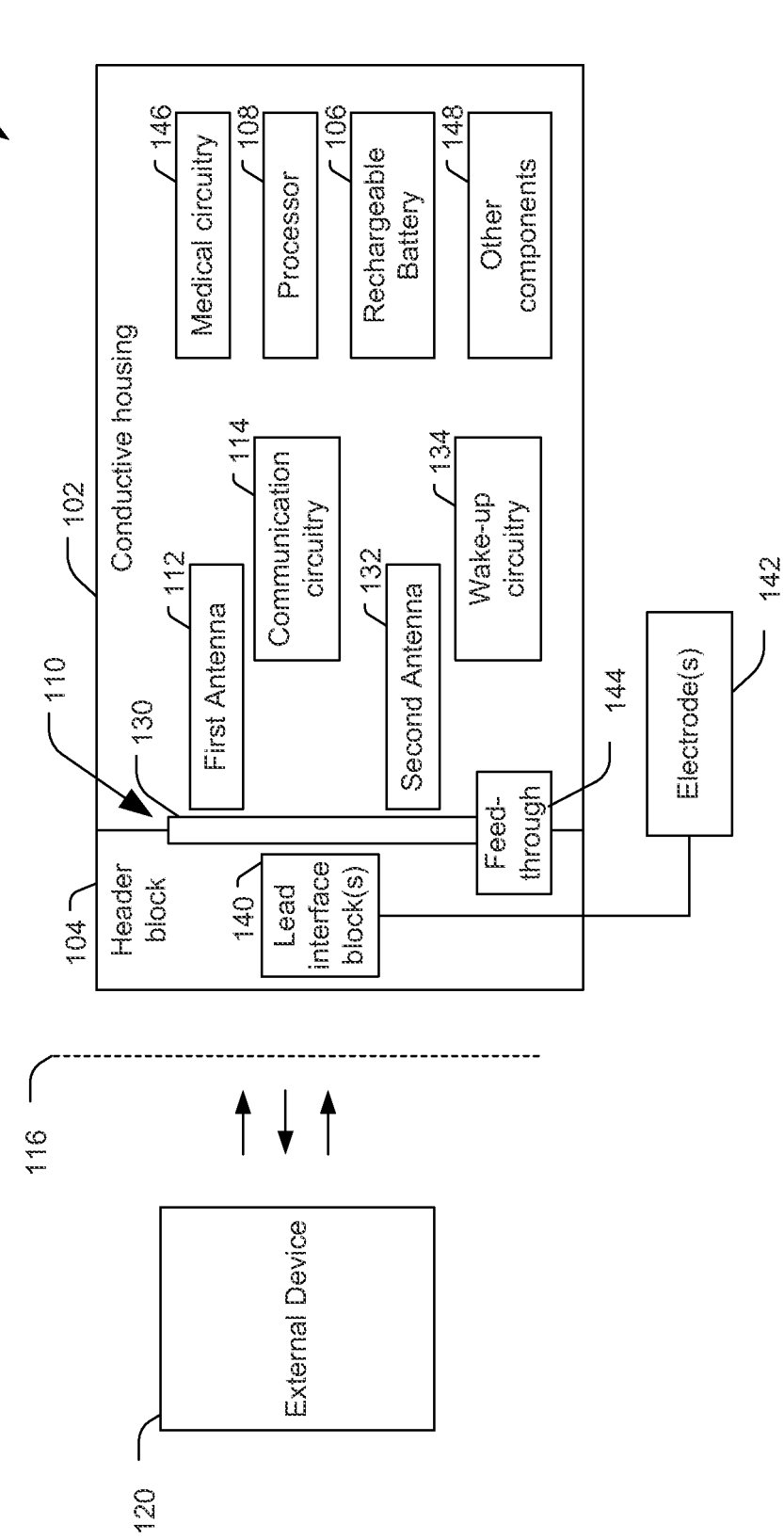
FIG. 1 is a block diagram of an implantable medical device and an external charging device according to a particular embodiment.

FIG. 1 is a block diagram of an implantable medical device (IMD) 100 and an external device 120 according to a particular embodiment. The IMD 100 may be implanted within a patient behind the tissue barrier 116 of the patient (e.g., the patient's skin and/or other tissue). In a particular embodiment, the IMD 100 includes the rechargeable battery 106. In another embodiment, the IMD 100 includes a different power source, e.g., a non-rechargeable battery. The IMD 100 may also include the processor 108. The processor 108 may be operable to control processes of the IMD 100, such as recharging of the battery, sensing or stimulation provided by medical circuitry 146, communication performed by communication circuitry 114, changing states of components of the IMD 100 in response to wake-up circuitry 134, other processes performed by other components 148 of the IMD 100, or any combination thereof.

The IMD 100 may also include a conductive housing 102 that defines an opening 110. The conductive housing 102 may be formed of a biocompatible material, such as a metal or metal alloy (e.g., Titanium or stainless steel). The IMD 100 may also include one or more antennas, such as a first antenna 112 and a second antenna 132 that are hermetically sealed within the conductive housing 102.

A dielectric material 130 may be coupled to the conductive housing 102 to hermetically seal the opening 110. Together, the dielectric material 130 and the conductive housing 102 form a case of the IMD 100. The dielectric material 130 may include a ceramic material, a polymer material or another dielectric material that is suitable to form a hermetic seal with the conductive housing 102. Hermetic seals between polymers and metals, such as the conductive housing 102, can be less reliable than hermetic seals between ceramics and metals. When the dielectric material 130 is a ceramic, the hermetic seal may be formed via a ceramic-to-metal sealing process, such as brazing or welding. One or more of the antennas 112, 132 may be positioned within the case behind the dielectric material 130. Without the opening 110, the conductive housing 102 may interfere with communication between an external device 120 and the first antenna 112, the second antenna 132, or both. The opening 110 hermetically sealed by the dielectric material 130 provides a signal path through the conductive housing 102, which results in significantly less signal strength reduction than would be experienced by attempting to transmit through the conductive housing 102.

The IMD 100 may include a header block 104. The header block 104 may be coupled to the case over the dielectric material 130. When the dielectric material 130 is formed of a relatively brittle material, such as ceramic, the header block 104 may be configured to retain pieces of the dielectric material 130 in an event of a catastrophic failure of the dielectric material 130. For example, the header block 104 may be formed of a first material that has a first mechanical failure mechanism (e.g., plastic deformation) when implanted within a patient, and the dielectric material 130 may be formed of a second material that has a second mechanical failure mechanism (e.g., shattering) when implanted within the patient. The second material may be more brittle at body temperature than the first material. Thus, the header block 104 may protect the dielectric material 130 against catastrophic failure by absorbing impact energy that would otherwise be absorbed by the dielectric material 130, potentially leading to shattering of the dielectric material. Additionally, the header block 104 may be coupled to the conductive housing 102 in a manner that causes the header block 104 to prevent pieces of the dielectric material 130 from being exposed to tissue of the patient. For example, the header block 104 may be coupled to the conductive housing 102 via a press fit, via one or more connectors (e.g., screws, rivets or snaps), via an adhesive, or via another polymer to metal joining process or technique.

The header block 104 may include lead interface blocks 140. The lead interface blocks 140 may be adapted to receive one or more electrode leads from electrodes 142. The lead interface blocks 140 may be coupled to the medical circuitry 146 within the conductive housing 102 via one or more hermetically sealed feedthroughs 144. The electrodes 142 may include stimulation electrodes, sensing electrodes, or a combination thereof. Likewise, the medical circuitry 146 may include therapeutic circuitry, sensing circuitry, or a combination thereof. In a particular embodiment, as further illustrated in FIG. 2, one or more of the lead interface blocks 140 may at least partially obscure one or more of the antennas 112, 132. Accordingly, one or more of the lead interface blocks 140 may be formed of a material that is suitable to provide electrical connection between the medical circuitry 146 and the electrodes 142, but does not significantly reduce signal strength of signals transmitted between the external device 120 and the particular antenna or antennas 112, 132 that may be partially obscured by the lead interface blocks 140. For example, the lead interface blocks 140 may be formed of stainless steel (e.g., 316L stainless steel), MP35N, or Titanium. In another embodiment, the lead interface blocks 140, the antennas 112, 132 may be positioned to limit interference of the lead interface blocks 140 with signals transmitted between the external device 100 and the antennas 112, 132.

The IMD 100 may include communication circuitry 114 within the case and coupled to the first antenna 112. The communication circuitry 114 may be operable to send signals to a device external to the conductive housing 102, such as the external device 120, to receive signals from the device external to the conductive housing 102, or both send and receive signals. For example, the communication circuitry 114 may be operable to transmit data to the external device 120. The transmitted data may include data gathered by medical circuitry in response to conditions detected by the electrodes 142 or data generated by the processor, such as data related to therapy provided to the patient or data related to a condition of the IMD (e.g., a charge state of the rechargeable battery 106, a case temperature of the IMD 100, or functionality of a component of the IMD 100). In another example, the communication circuitry 114 may be operable to receive data from the external device 120. The received data may include stimulation therapy parameters, activation signals to activate one or more of the other components 148 of the IMD 100, other data, or a combination thereof.

The IMD 100 may include wake-up circuitry 134 within the conductive housing 102. The wake-up circuitry 134 may be coupled to the second antenna 132. The wake-up circuitry 134 may be operable, in response to a wake-up signal received at the second antenna 132, to cause the communication circuitry 114 to transition from a sleep state in which the communication circuitry 114 is inactive to an awake state in which the communication circuitry 114 is active. In a particular embodiment, the wake-up circuitry 134 may awaken another or a different component of the IMD 100 in response to the wake-up signal. For example, the communication circuitry 114, the processor 108, the medical circuitry 146, one or more of the other components 148, or a combination thereof, may transition to a sleep state at particular times to conserve power or for other purposes. The wake-up signal may be used to awaken any component of the IMD 100 to which the wake-up signal is directed. To illustrate, the communication circuitry 114 may enter the sleep state when no communication has been received from the external device 120 for a particular period of time. To awaken the communication circuitry 114 (e.g., to transmit a new therapy program to be implemented by the IMD 100), the external device 120 may first transmit the wake-up signal and wait for an acknowledgement from the communication circuitry 114 indicating that the communication circuitry 114 is in the active state before transmitting additional data.

In a particular embodiment, the first antenna 112 is a planar antenna. Use of a planar antenna may be beneficial where available space is constrained, such as within the conductive housing 102. For example, the first antenna 112 may include one or more conductive elements disposed on a circuit board. To illustrate, the first antenna 112 may be a loop or coil-type antenna disposed on the circuit board. In another illustrative example, the first antenna 112 may be a slot-type antenna including a conductive layer on a surface of the circuit board. The conductive layer may define a radiating slot.

In a particular embodiment, the second antenna 132 may be arranged to receive the wake-up signal through the first antenna 112. To illustrate, when the first antenna is a slot-type antenna, the wake-up signal may propagate through the opening 110 and through the radiating slot of the first antenna 112 to be received by the second antenna 132. Thus, space within the IMD 100 may be further conserved by positioning the second antenna 132 in an open area of the first antenna 112, allowing both the first antenna 112 and the second antenna 132 to transmit and/or receive signals through the opening 110 and the dielectric material 130.

Figure 2:
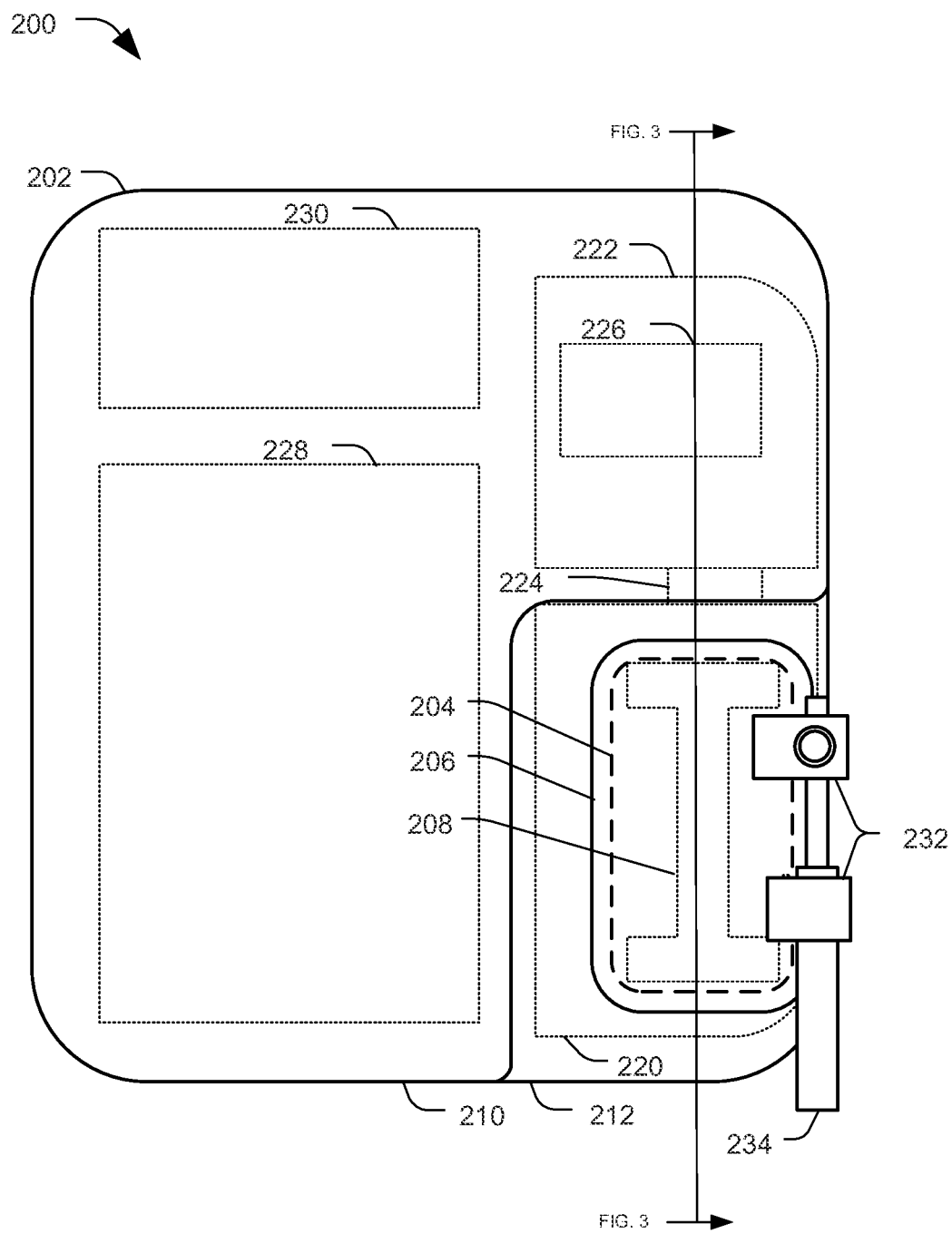
FIG. 2 is a schematic illustration of a top view of an implantable medical device with a header block removed according to a particular embodiment.
Figure 3:
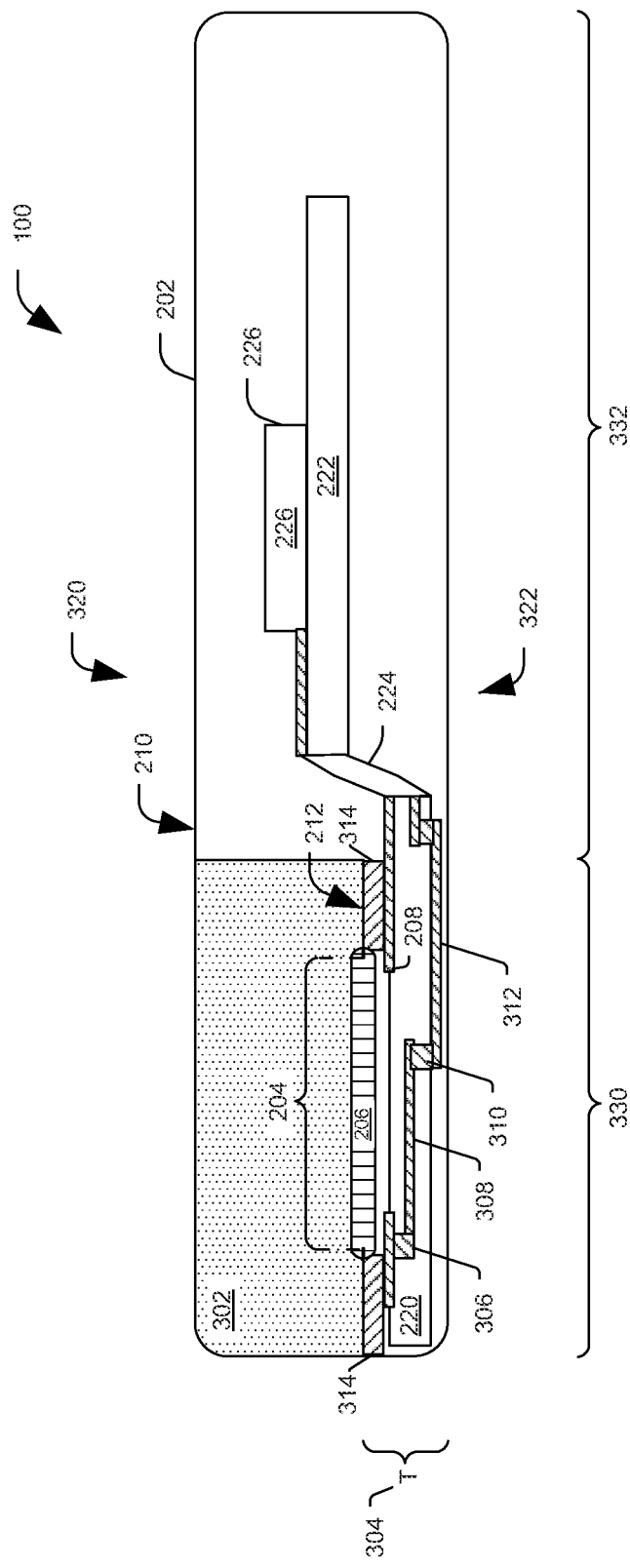
FIG. 3 is a schematic illustration of a cutaway side view of an implantable medical device according to a particular embodiment.

FIG. 2 is a schematic illustration of a top view of an implantable medical device (IMD) 200. FIG. 3 is a cutaway side view of the IMD 200 along a section line shown in FIG. 2. In the view depicted in FIG. 2, components internal to a conductive housing 202 of the IMD 100 are shown in dotted lines. Additionally, while FIG. 3 shows a header block 302, the header block 302 is not shown in FIG. 2.

The IMD 200 includes a power source, such as a battery 228. For example, the battery 228 may be a rechargeable battery, such as the rechargeable battery 106 of FIG. 1. The IMD 200 may also include functional circuitry 230 such as medical circuitry (e.g., therapeutic circuitry, sensing circuitry or both), a processor, memory, charging circuitry, other components or a combination thereof. The medical circuitry of the functional circuitry 230 may be coupled to one or more lead interface blocks 232 external to the conductive housing 202 via one or more hermetically sealed feedthroughs (not shown in FIG. 2). The lead interface blocks 232 may be adapted to receive an electrode lead 234. The electrode lead 234 may be coupled to an electrode (not shown in FIG. 2) that is coupled to or positioned proximate to tissue of a patient that is to be stimulated or from which data is to be sensed.

The IMD 200 may also include communication circuitry 226. For example, the communication circuitry 226 may include a receiver, a transmitter, a transceiver, a coder/decoder (CODEC), other components that operate to facilitate communication between the IMD 200 and a device external to the patient, or a combination thereof. The communication circuitry 226 may be coupled to one or more antennas, such as an antenna 208. Other examples of antennas and communication circuitry are described with reference to FIGS. 4A-4E.

In a particular embodiment, the conductive housing 202 of the IMD 200 may be hermetically sealed. The conductive housing 202 may define an opening 204 which may be hermetically sealed with a dielectric material 206. For example, the dielectric material 206 may fill the opening 204 and extend past edges of the opening 204 to form a seal with the conductive housing 202. In a particular embodiment, the dielectric material 206 is a ceramic material that is sealed to the conductive housing 202 using a ceramic-to-metal brazing or welding process.

The antenna 208 may be positioned within the conductive housing 202 behind the dielectric material 206. In a particular embodiment, at least one dimension of the opening 204 (e.g., a length, a width, or both) is larger than a corresponding dimension of a radiating element of the antenna 208. For example, in the particular embodiment illustrated in FIG. 2, the antenna 208 is a slot-type antenna and the radiating element is shown as an "I" shape cutout of a conductive layer. Thus, at least one dimension of the opening 204 may be larger than a corresponding dimension of the "I" shaped cutout in the conductive layer.

For ease of implantation in a patient and for comfort of the patient, it may be desirable for the IMD 200 to have a relatively small form factor. Accordingly, the header block 302 (in FIG. 3) may be positioned within a recess of the conductive housing 202. To illustrate, as shown in FIG. 3, the conductive housing 202 has a first side 320 and a second side 322 opposite the first side 320. The first side 320 may have a recessed portion 212 (under the header block 302) and a non-recessed portion 210. A distance between non-recessed portion 210 and the recessed portion 212 of the first side 320 is smaller than a second distance between the second side 322 and the non-recessed portion 210 of the first side 320 by a thickness, T, 304. The header block 302 may extend from the recessed portion 212 of the first side 202 to approximately flush with the non-recessed portion 210 of the first side 202, thus providing a relatively small form factor such that the header block 302, which houses the lead interface blocks 232, blends relatively smoothly with the conductive housing 202. The antenna 208 may be positioned between the second side 322 and the recessed portion 212 of the first side 320 in a first region 330 with the thickness T 304. Other components of the IMD 100 may be positioned in a second region 332 with a thickness greater than the thickness T 304.

To enable the antenna 208 to fit in the first region 330, the antenna 208 may be relatively thin, such as a planar antenna. In a particular embodiment, the antenna 208 is formed on a first circuit board 220 that can be positioned in the first region 330 by sliding the first circuit board 220 (or a portion of the first circuit board 220) into the first region 330. To simplify assembly of the IMD 100, the communication circuitry 226 may be coupled to a second circuit board 222 that is communicatively coupled to the first circuit board 220 via a flexible circuit 224. Various configurations of the first circuit board 220, the second circuit board 222 and the flexible circuit 224 are illustrated in FIGS. 4A-4E.

In a particular embodiment, circuitry that supports the antenna 208 may also be formed on or coupled to the first circuit board 220. For example, the first circuit board 220 may include multiple layers. The antenna 208 may include a conductive layer formed on or coupled to an upper surface (in the orientation depicted in FIG. 3) of the circuit board 220. A feed line 308 may be formed on the upper surface of the circuit board 220, on a lower surface of the circuit board 220 or between layers of the circuit board 220 (e.g., interior to the circuit board 220). When the feed line 308 is on a different layer of the circuit board 220 than the antenna 208, the feed line 308 may be coupled to the antenna 208 by a conductive via 306. Other components that support functionality of the antenna 208 may also be formed on or coupled to the circuit board 220, such as matching components 312. The matching components 312 may include inductive elements, capacitive elements or other elements that facilitate impedance matching of the antenna 208, the feed line 308 and other communication components, such as the communication circuitry 226. When the feed line 308 and the matching components 312 are on different layers of the circuit board 220, the matching components 312 may be coupled to the feed line 308 by a conductive via 310.

In a particular embodiment, an insulating layer 314 may be positioned between the antenna 208 and an interior of the conductive housing 202 in at least the first region 330. The insulating layer 314 may inhibit or prevent the antenna 208 from shorting out against the conductive housing 202. In a particular embodiment, the dielectric material 206 may extend into the conductive housing 202 such that the antenna 208 is prevented from contacting the conductive housing 202 by the dielectric material 206. The insulating layer 314 may not be present in this embodiment.

Positioning the antenna 208 within the conductive housing 202, as opposed to external to the conductive housing 202, enables elimination of connective elements to connect the antenna 208 to the communication circuitry 226. Such connective elements tend to be bulky, failure prone and difficult to work with during manufacturing of an IMD. The conductive housing 202 may reduce performance of the antenna 208 when the antenna 208 is positioned within the conductive housing 202. Providing the opening 204 that is hermetically sealed with the dielectric material 206 reduces or eliminates interference of the conductive housing 202 with communications via the antenna 208. The header block 302 protects the dielectric material 206 from damage and protects the patient from pieces of the dielectric material 206 in the event of catastrophic failure of the dielectric material 206. Thus, effective communications may be provided safely, at low manufacturing cost, and in a relatively small form factor IMD 100 by positioning the antenna 208 within the conductive housing 202 beneath the dielectric material 206 and the header block 302.

FIGS. 4A-4E are schematic illustrations of antenna systems for use inside an implantable medical device (IMD) according to various embodiments. The antenna systems illustrated in FIGS. 4A-4E each use a two circuit board configuration with the antenna 208 on the first circuit board 220 and the communication circuitry 226 on the second circuit board 222. The first circuit board 220 may be coupled to the second circuit board 222 by the flexible circuit 224. Other configurations of the antenna 208 and the communication circuitry 226 may be used, such as the antenna 208 and the communication circuitry 226 on a single circuit board, the communication circuitry 226 distributed across two or more circuit boards, or coupling the communication circuitry 226 to the antenna 208 using discrete wires rather than the flexible circuit 224. Thus, in FIGS. 4A-4E, the two circuit board configuration is used in order to better highlight other differences between the illustrated embodiments.

In a particular embodiment, at least the first circuit board 220 may have multiple layers. Portions of or components of the antenna system may be formed on or positioned on different layers of the first circuit board 220. FIGS. 4A-4E are illustrated as top views of the various embodiments of the antenna system with components on a top layer depicted with solid lines, components on a middle or interior layer depicted with dashed lines, and components on a bottom layer depicted with dotted lines. The particular arrangements of components on layers of the first circuit board 220 depicted in FIGS. 4A-4E are only illustrative and other arrangements are envisioned. For example, to save manufacturing cost, all components of the antenna system may be located on exterior surfaces of the circuit boards 220, 222, with no components located on the middle or interior layers. Additionally, in FIGS. 4A-4E, the antenna 208 is illustrated as a slot-type antenna including a conductive layer 402 on the top surface of the first circuit board 220, where the conductive layer 402 defines a radiating slot with an "I" shape. Other antenna configurations may be used. For example, other types of planar antenna may be used rather than a slot-type antenna, such as a dipole antenna, an inverted F antenna, a loop antenna, a coil antenna, a microstrip or patch antenna. Additionally, when a slot-type antenna is used, other shapes of the radiating slot may be used, such as one or more rectangular slots, a bow tie slot, an inverted "E" shaped slot, or another slot optimized for performance for a particular configuration of the IMD. The planar antennas may include conductive elements disposed on the first circuit board 220. A non-planar antenna may also be used so long as the non-planar antenna is configured to be positioned within a conductive housing of an IMD beneath an opening in the conductive housing (as described with reference to FIGS. 2 and 3).

Figure 4C:
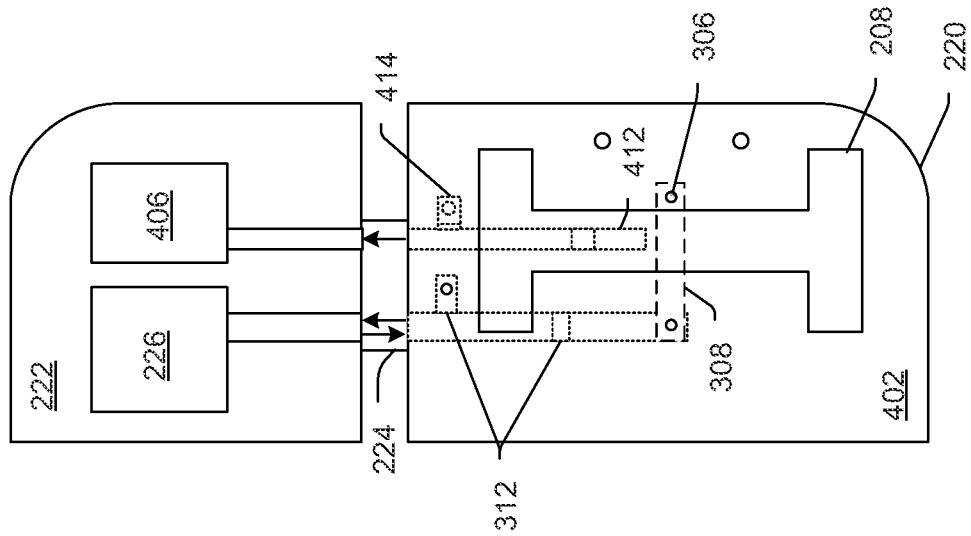
FIGS. 4A-4E are schematic illustrations of antenna systems for use inside an implantable medical device according to various embodiments.
Figure 4B:
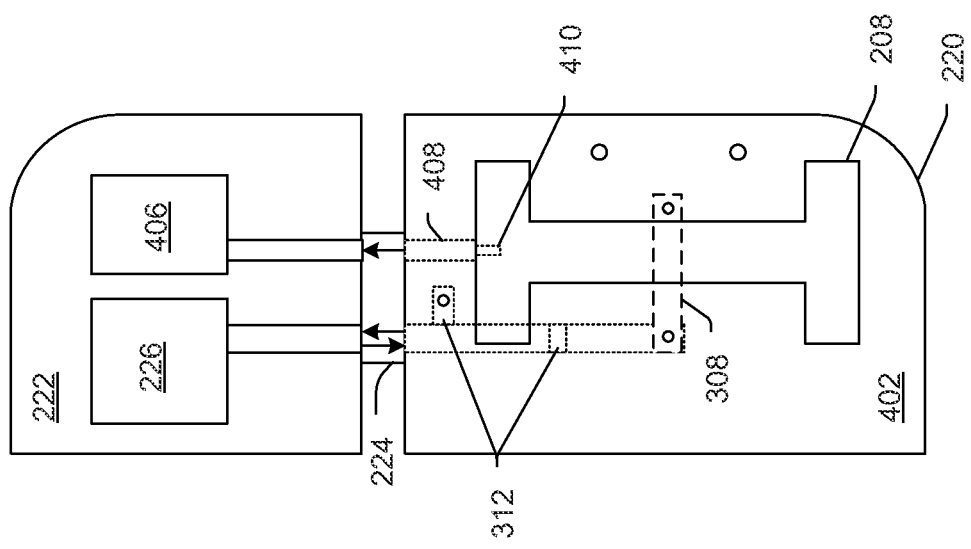
Figure 4A:
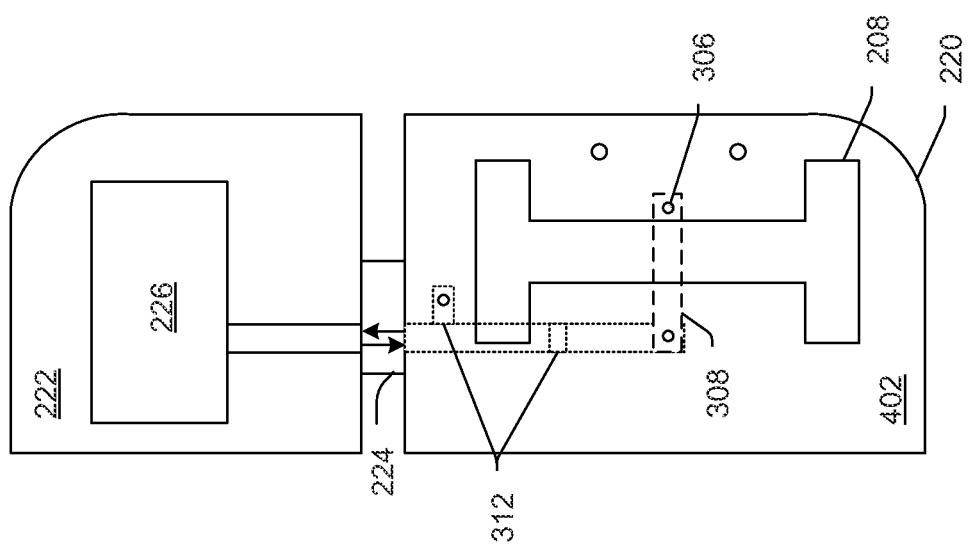

FIG. 4A depicts a top view of a first embodiment of an antenna system. As explained above, the antenna system includes the first circuit board 220 including the antenna 208 and the second circuit board 222 including the communication circuitry 226. The first circuit board 220 is coupled to the second circuit board 222 by the flexible circuit 224. The antenna 208 is coupled to the feed line 308 by the conductive via 306 and the matching components 312 are coupled to the feed line 308.

In FIG. 4B, a second antenna 410 is added to the antenna system depicted in FIG. 4A. In the view depicted in FIG. 4B, the second antenna 410 is positioned within the radiating slot of the antenna 208 (also referred to herein as the "first antenna" to distinguish from the second antenna 410). In a particular embodiment, the second antenna 410 may be located on a bottom layer of the first circuit board 220 and the first antenna 208 may be located on a top layer of the first circuit board 220. The second antenna 410 may be a surface-mountable chip antenna and may be housed in a small form-factor ceramic or polymer package. In another embodiment, the antenna 208 is positioned on the same side of the circuit board 120 or on another layer of the circuit board 120 relative to the second antenna 410. In other embodiments, the second antenna 410 is not positioned behind the opening 130 of the conductive housing 102, is not positioned within or behind the radiating slot of the first antenna 208, or both.

In the embodiment illustrated in FIG. 4B, the first antenna 208 may be a primary communication antenna and the second antenna 410 may be a wake-up antenna. For example, the second antenna 410 may be used to receive a wake-up signal from a device external to a patient in which an IMD is implanted. In response to the wake-up signal, the wake-up circuitry 406 may cause the communication circuitry 226 to transition from a sleep state in which the communication circuitry 226 is inactive to an awake state in which the communication circuitry 226 is active. The communication circuitry 226 may then send signals to and receive signals from the device external to the patient or care provider. For example, the communication circuitry 226 may use the first antenna 208 to send information regarding sensed conditions within the patient or within the IMD to the device external to the patient. In another example, the communication circuitry 226 may receive information from the device external to the patient via the first antenna 208 to program the IMD to perform various therapeutic functions, such as providing stimulation to the tissue of the patient. Alternatively, the first antenna 208 may be the wake-up antenna and the second antenna 410 may be the primary communication antenna.

When the antenna system illustrated in FIG. 4B is positioned in the conductive housing 202 of the IMD 100 of FIGS. 2 and 3, the wake-up signal may propagate through the opening 204 and through the radiating slot of the first antenna 208 to be received by the second antenna 410. Thus, positioning the second antenna 410 within the radiating slot of the first antenna 208 further enables efficient use of space within the IMD 100. The second antenna 410 may be a surface mountable component, such as a ceramic antenna, or it may be a planar antenna.

The embodiment illustrated in FIG. 4C depicts another configuration of a second antenna 412. In the embodiment illustrated in FIG. 4C, the second antenna 412 may include a conductive element (e.g., a metal layer) formed on or coupled to a layer of the first circuit board 220. For example, the second antenna 412 may be formed on or coupled to the bottom layer of the first circuit board 220. Second matching components 414 may be coupled to the second antenna 412 to improve performance of the second antenna 412 at a frequency of the wake-up signal. For example, the matching components 312 may facilitate communications of the first antenna 208 at a frequency of about 400 MHz and the second matching components 414 may facilitate communications of the second antenna 412 at a frequency of about 2.45 GHz.

Figure 4E:
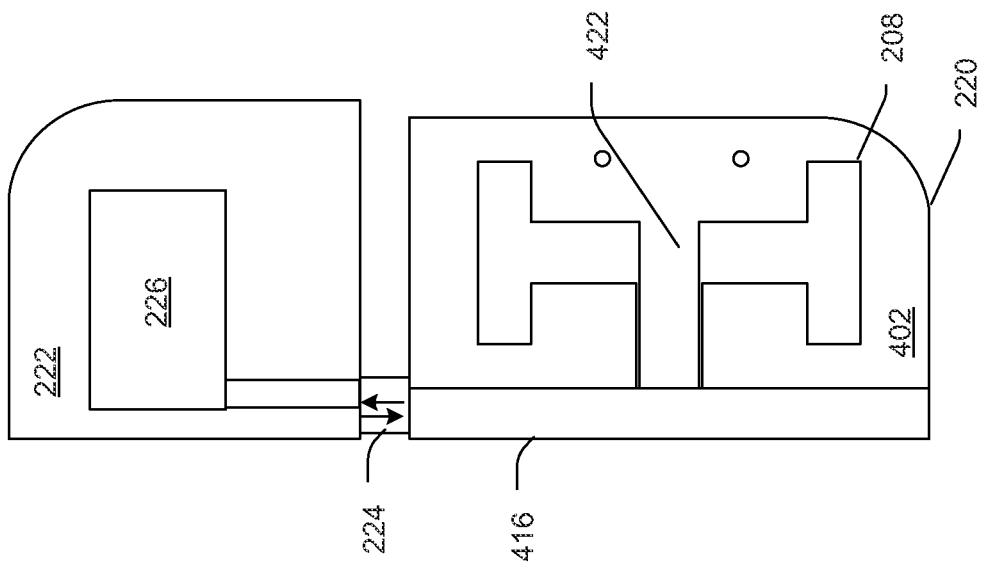
Figure 4D:
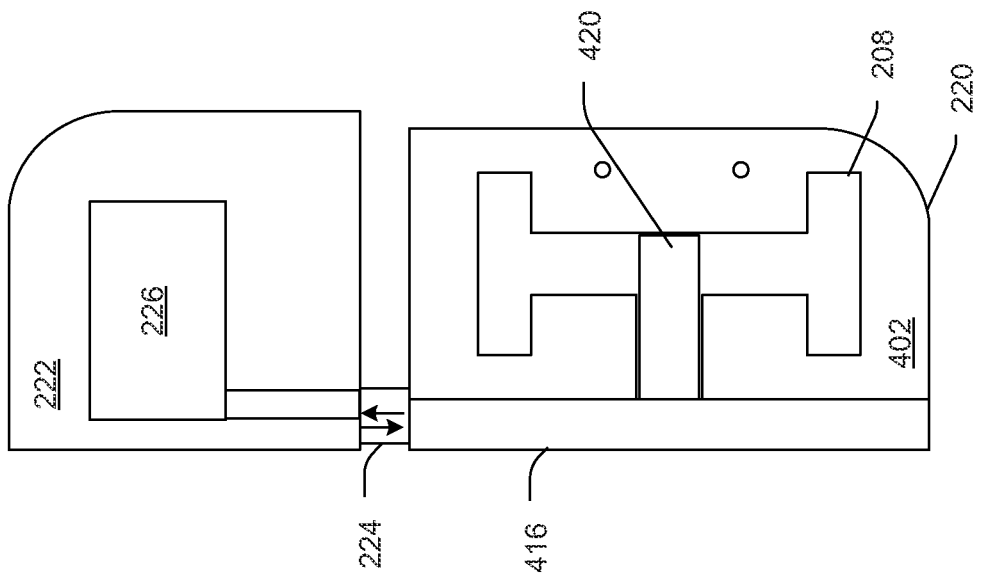

FIGS. 4D and 4E illustrate embodiments in which a feed line of the first antenna is located on the same surface of the first circuit board 220 as the first antenna 208. In FIGS. 4D and 4E, the first antenna 208 includes the conductive layer 402 on the top surface of the first circuit board 220 and a communication line 416 is located on the top surface of the first circuit board 220. In FIG. 4D, the communication line 416 couples an open ended feed line 420, located on the top surface of the first circuit board 220, to the communication circuitry 226. In FIG. 4E, the communication line 416 couples a shorted feed line 420 located on the top surface of the first circuit board 220, to the communication circuitry 226.

The embodiments illustrated in FIGS. 4D and 4E may also be used with a second antenna, such as the second antenna 410 of FIG. 4B or the second antenna 412 of FIG. 4C. When the second antenna is present, the second antenna may be located on the same side of the first circuit board 220 as the first antenna or on an opposite side.

Figure 5:
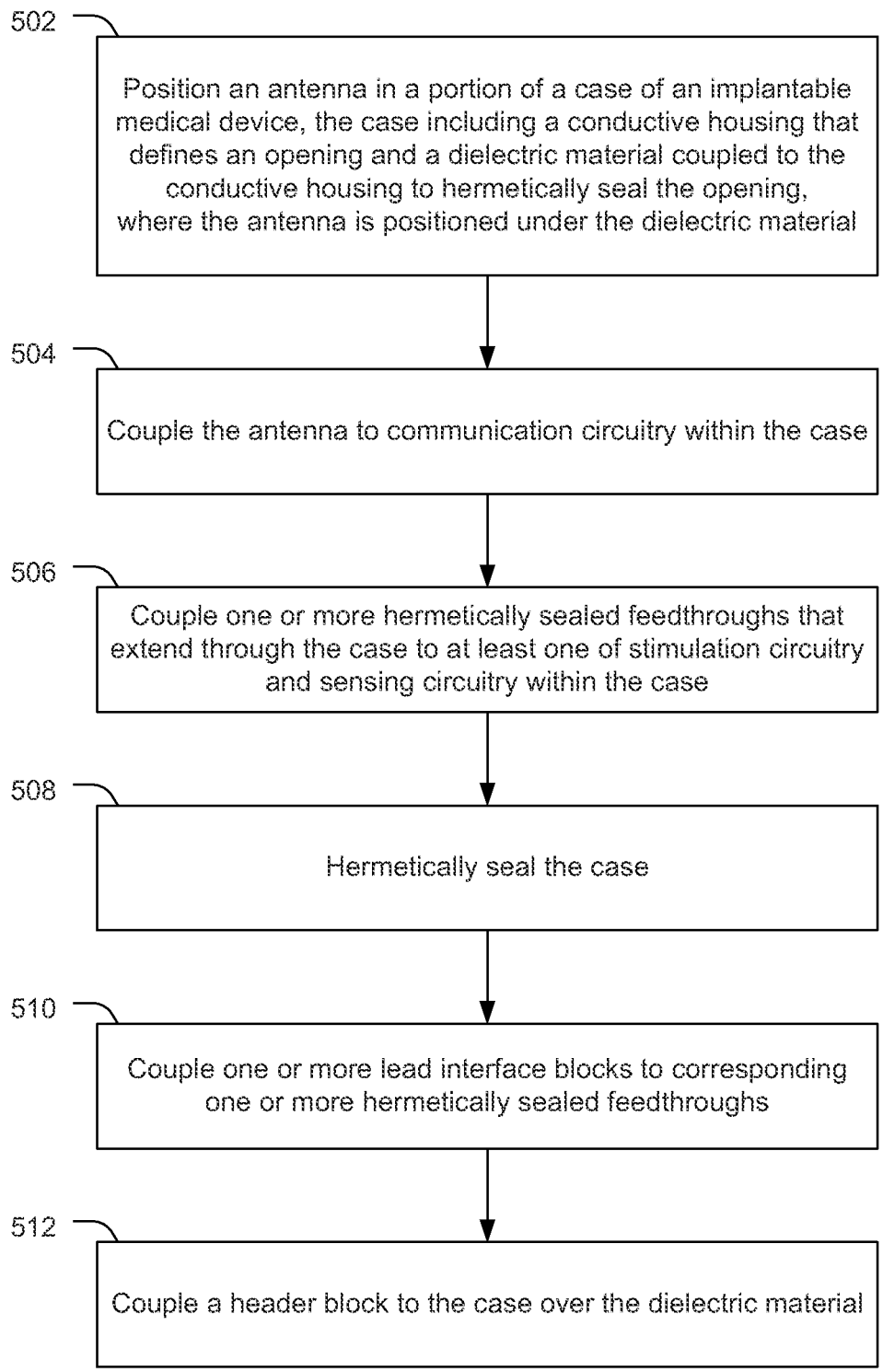
FIG. 5 is a flow chart of a method of manufacturing an implantable medical device according to a particular embodiment.

FIG. 5 is a flow chart of a method of manufacturing an implantable medical device (IMD) according to a particular embodiment. The method may be used to manufacture the IMD 100 of FIG. 1 or the IMD 200 of FIGS. 2 and 3. The method may include, at 502, positioning an antenna in a portion of a case of the IMD. The case may include a conductive housing that defines an opening. A dielectric material may be coupled to the conductive housing to hermetically seal the opening, and an antenna may be positioned under the dielectric material.

The method may also include, at 504, coupling the antenna to communication circuitry. For example, the antenna may include the first antenna 112 of FIG. 1, which may be coupled to the communication circuitry 105. In another example, the antenna may include the second antenna 132, which may be coupled to the wake-up circuitry 134. In still another example, the antenna may include one of the antennas 208, 410 or 412 of FIG. 2, 3, or 4A-4E, which may be coupled to the communication circuitry 226 or the wake-up circuitry 406 via the flexible circuit 224.

The method may include, at 506, coupling one or more hermetically sealed feedthroughs that extend through the case to at least one of stimulation circuitry and sensing circuitry within the case. For example, the one or more hermetically sealed feedthroughs may include the feedthroughs 144 of FIG. 1. In this example, the feedthroughs 144 may be coupled to the medical circuitry 146, which may include sensing circuitry, other circuitry related to gathering data or providing therapy to a patient, or any combination thereof. The feedthroughs may extend through the dielectric material, through the conductive housing, or one or more of the feedthroughs may extend through the dielectric material and one or more of the feedthroughs may extend through the conductive housing.

The method may include, at 508, hermetically sealing the case. For example, the conductive housing of the case may include multiple pieces which may be coupled together to form a hermetic seal. The pieces of the conductive housing may be welded, brazed, soldered, adhered or otherwise sealed together.

The method may include, at 510, coupling one or more lead interface blocks to corresponding one or more hermetically sealed feedthroughs. For example, the lead interface blocks may include the lead interface blocks 140 of FIG. 1 which are coupled through the feedthroughs 144 to the medical circuitry 146 within the conductive housing 102. In another example, the lead interface blocks may include the lead interface blocks 232 of FIG. 2, which may be coupled to circuitry 230 within the conductive housing 202 via one or more hermetically sealed feedthroughs (not shown). The lead interface blocks may be coupled to the corresponding hermetically sealed feedthroughs before the case is sealed or after the case is sealed.

The method may include, at 512, coupling a header block to the case over the dielectric material. For example, the header block may include the header block 302 of FIG. 3. In a particular embodiment, the header block may be coupled to the case at the same time the lead interface blocks are coupled to the feedthroughs. For example, lead interface blocks may be embedded within or integral with the header block such that positioning the header block also positions the lead interface blocks.

Figure 6:
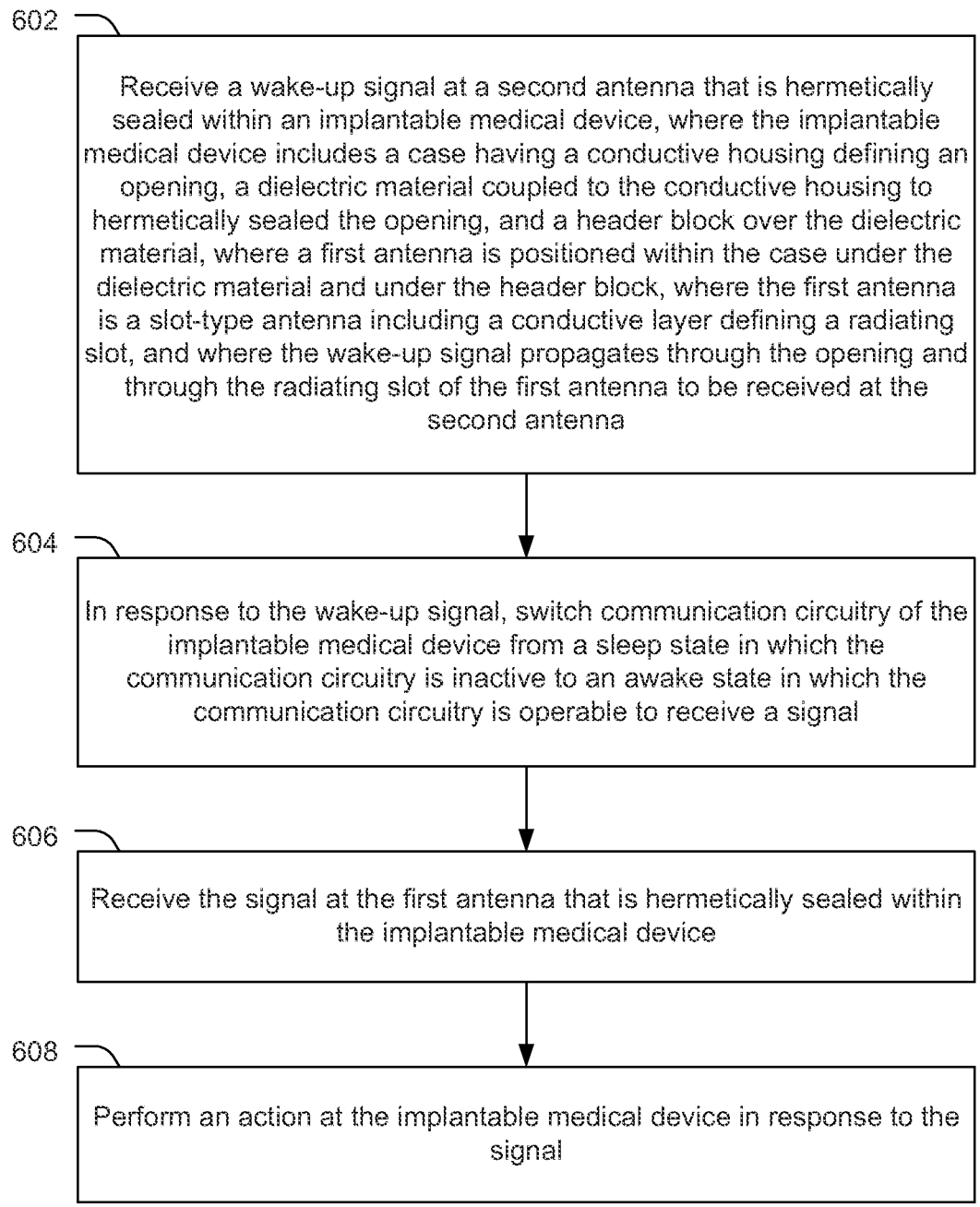
FIG. 6 is a flow chart of a method of communicating with an implantable medical device according to a particular embodiment.

FIG. 6 is a flow chart of a method of communicating with an implantable medical device (IMD) according to a particular embodiment. The method may be performed by the IMD 100 of FIG. 1 or the IMD 200 of FIGS. 2 and 3. The method may include, at 602, receiving a wake-up signal at a second antenna that is hermetically sealed within the IMD. For example, the IMD may be the IMD 100 of FIG. 1 or the IMD 200 of FIGS. 2 and 3, and the second antenna may correspond to the second antenna 132 of FIG. 1, the wake-up antenna 410 of FIG. 4B or the wake-up antenna 412 of FIG. 4C. The IMD may include a case having a conductive housing that defines an opening. A dielectric material may be coupled to the conductive housing to hermetically seal the opening and a header block may be located over the dielectric material. A first antenna and the second antenna may be positioned within the case under the dielectric material and under the header block. In a particular embodiment, the first antenna is a planar antenna, such as a slot-type antenna or another planar antenna. To illustrate, the first antenna may include a conductive layer defining a radiating slot. In this example, the second antenna may be positioned within or beneath the radiating slot. Thus, the wake-up signal may propagate through the opening of the conductive housing and through the radiating slot of the first antenna to be received at the second antenna.

In response to the wake-up signal, communication circuitry of the IMD may be switched from a sleep state in which the communication circuitry is inactive to an awake state in which the communication circuitry is operable to receive signals, at 604. In a particular embodiment, the communication circuitry may transition to the awake state in response to a signal received at the first antenna or in response to another event, such as passage of a particular period of time. In this embodiment, the IMD may not include the second antenna. For example, only the first antenna may be positioned within the case under the dielectric material and under the header block.

The method may include, at 606, receiving a signal at the first antenna, which is hermetically sealed within the IMD. The IMD may perform an action in response to the signal, at 608. For example, the IMD may deliver electrical stimulation to neural tissue of a patient. In another example, the IMD may sense a condition of the patient (e.g., a heart rate) or of the IMD (e.g., a battery charge level).

Figures 7A, 7B:
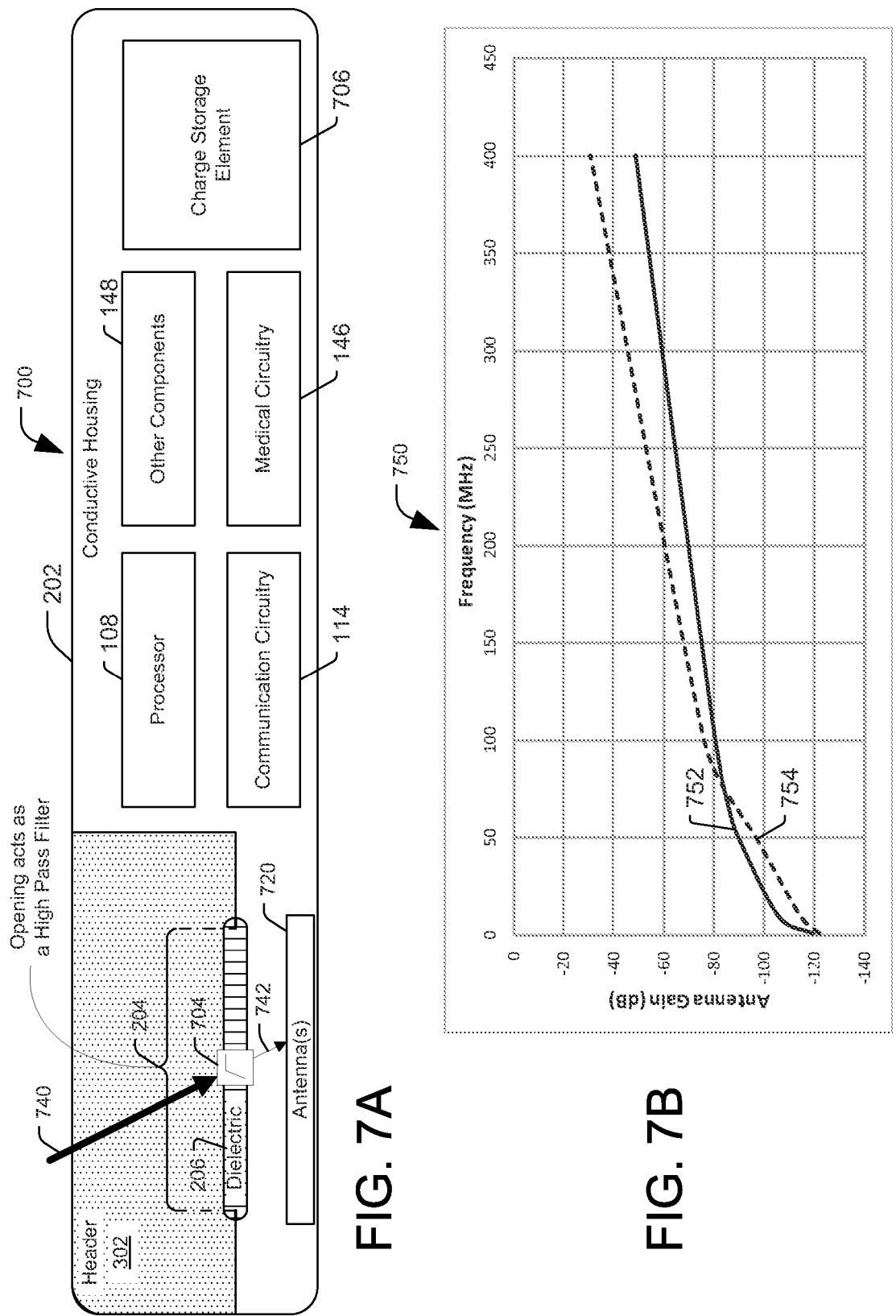
FIGS. 7A-7B include a schematic illustration of a cutaway side view of an implantable medical device and a graph illustration of antenna gain according to a particular embodiment.

FIGS. 7A-7B include a schematic illustration of a cutaway side view of an implantable medical device (IMD) 700 and a graph 750 illustrating antenna gain according to a particular embodiment. The IMD 700 may include a case having a conductive housing 202. In a particular embodiment, the conductive housing 202 of the IMD 700 may be hermetically sealed. The conductive housing 202 may define an opening 204 which may be hermetically sealed with a dielectric material 206. For example, the dielectric material 206 may fill the opening 204 and extend past edges of the opening 204 to form a seal with the conductive housing 202. In a particular embodiment, the dielectric material 206 is a ceramic material that is sealed to the conductive housing 202 using a ceramic-to-metal brazing or welding process.

A header block 302 may be coupled to the conductive housing 202 of the case over the dielectric material 206. The header block 302 may be coupled to the conductive housing 202 via a press fit, via one or more connectors (e.g., screws, rivets or snaps), via an adhesive, or via another polymer to metal joining process or technique.

The IMD 700 may include a charge storage element 706, such as a battery, a rechargeable battery, or a capacitor. The IMD 700 may also include functional circuitry, such as a processor 108, medical circuitry 146, and other components, or a combination thereof. The IMD 700 may also include communication circuitry 114. For example, the communication circuitry 114 may include a receiver, a transmitter, a transceiver, a coder/decoder (CODEC), other components that operate to facilitate communication between the IMD 700 and a device external to the patient, or a combination thereof. The communication circuitry 114 may be coupled to one or more antennas, such as an antenna(s) 720. The one or more antennas may be used for data communication, to wake-up the IMD 700, to wirelessly power the IMD 700 using far-field radiative powering signals, or any combination thereof.

The antenna(s) 720 may be positioned within the conductive housing 202 behind the dielectric material 206. In a particular embodiment, at least one dimension of the opening 204 (e.g., a length, a width, or both) is larger than a corresponding dimension of a radiating element of the antenna(s) 720. For example, in the particular embodiment illustrated in FIG. 7A, the antenna 720 is a slot-type antenna and the radiating element is shown as an "I" shape cutout of a conductive layer. Thus, at least one dimension of the opening 204 may be larger than a corresponding dimension of the "I" shaped cutout in the conductive layer.

In a particular embodiment, there are no high pass antenna feedthroughs extending through the case (e.g., the dielectric material 206 in the opening 204) into the header block 302 for the antenna(s) 720. In another particular embodiment, there are no antenna feedthroughs extending through the case (e.g., the dielectric material 206 in the opening 204) into the header block 302 for the antenna(s) 720. The physical structure of the antenna(s) 720 does not extend through the conductive housing 202 or the dielectric material 206. In addition, the antenna(s) 720 may be configured to not be electrically connected to the conductive housing 202. For example and insulating layer 314, as shown in FIG. 3, or a space may separate the antenna(s) 720 from the conductive housing 202. One issue that may arise if the antenna is electrically coupled to the conductive housing is that the conductive housing may introduce a significant amount of noise that will negatively impact the signal-to-noise ratio of the RF communication. For example, if a slot was formed in the conductive housing and electrically connected to the communication circuitry to form a slot antenna out of the conductive housing, the conductive housing would expose the communication circuitry a lot of outside noise. Therefore, it may be beneficial to not electrically connect the antenna to the conductive housing.

In a particular embodiment, the opening 204 may be used as a high pass filter as illustrated by the high pass filter block 704. The opening 204 may receive signals 740 at a variety of frequencies and permit only frequencies 742 above a frequency from being substantially attenuated. The frequency at which the attenuation become significant or substantial (e.g., the cutoff frequency) may be determined, at least in part, by the dimensions of the opening 204. In general, the smaller the dimensions of the opening, the higher the cutoff frequency. FIG. 7B is a graph 750 illustrating the antenna gain of an IMD having an opening in the conductive housing, trace 754, and an IMD with the top of the conductive housing removed so as to expose the antenna and additional circuitry, trace 752. In the particular embodiment illustrated in FIG. 7B, the trace 754 shows an antenna gain approximately 3 dB higher than trace 752 at approximately 100 MHz. The separation between the antenna gain of trace 754 and trace 752 continues to increase as the frequency increases. At approximately 400 MHz, the different in antenna gain between the two traces is approximately 18 dB.

In a particular embodiment, no high pass filter antenna feedthrough is used to assist in attenuating lower frequency signals. However, the opening 204 may be appropriately sized and used as a high pass filter to assist in attenuating the lower frequency signals as illustrated in FIGS. 7A and 7B.

Figure 8A:
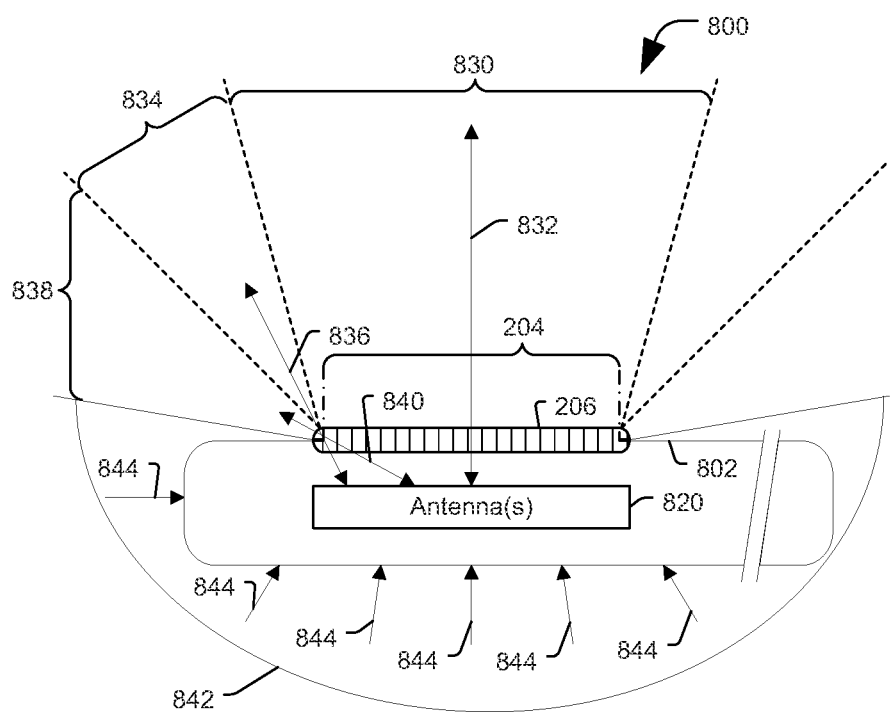
FIGS. 8A-8B are schematic illustrations of cutaway side views of an implantable medical device according to a particular embodiment.
Figure 8B:
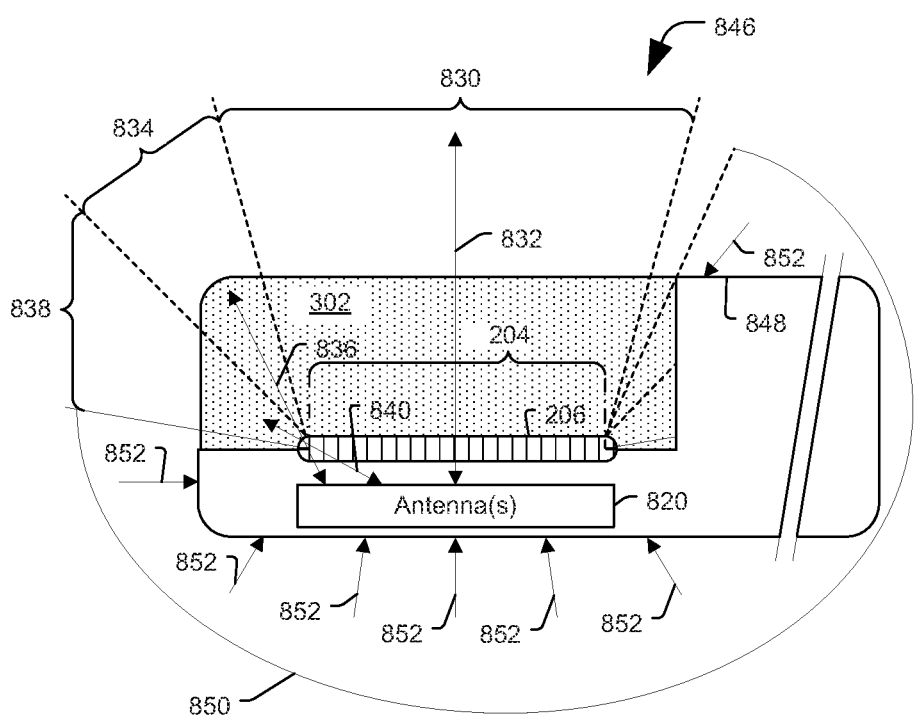

FIGS. 8A-8B are schematic illustrations of cutaway side views of implantable medical devices (IMD) 800 and 846 according to particular embodiments. The IMD 800 includes a case having a conductive housing 820, an opening 204 defined by the conductive housing 802, a dielectric material 206 to hermetically seal the opening 204, and an antenna(s) 820 positioned within the conductive housing 202 behind the dielectric material 206. In a particular embodiment, at least one dimension of the opening 204 (e.g., a length, a width, or both) is larger than a corresponding dimension of a radiating element of the antenna(s) 820.

The antenna(s) 820 may be configured to transmit and receive signals to and from one or more external devices. Lines have been drawn around the IMD 800 to illustrate various zones, including three line-of-sight zones 830, 834, and 838, and one out-of-sight zone 842. The three line-of-sight zones 830, 834, and 838 are zones in which the antenna(s) 820 is within line-of-sight through the opening 204 to the external transmitting or receiving device. Zone 830 represents signals 832 that are substantially orthogonal to the antenna(s) 820. The signal strengths of these orthogonal signals 832 should be close to maximum. Zone 834 represents signals 836 that are still in line-of-sight and slightly off of substantially orthogonal. The signal strength of these slightly off of orthogonal signals 836 should be slightly below maximum. Zone 838 represents signals 840 that are still in line-of-sight but are off of orthogonal. The signal strength of these off of orthogonal signals 840 should be lower than both the substantially orthogonal signals 832 and the slightly off of orthogonal signals 836. Zone 842 represents signals 844 that are not within line-of-sight of the antenna(s) 820. The conductive housing 802 of the case blocks the signals 844 from being received by the antenna(s) 820. The lines depicting the line-of-sight zones are provided to illustrate that there is some variation of signal strength based on the angle of the signal in relation to the antenna(s) 820 and should not be construed to be limiting. Providing the antenna(s) 820 within the conductively housing provides a more directional antenna configuration and reduces the interference seen at the antenna(s) 820 from unwanted signals.

Referring to FIG. 8B, the IMD 846 includes a case having a conductive housing 846, an opening 204 defined by the conductive housing 848, a dielectric material 206 to hermetically seal the opening 204, a header 302 positioned over the dielectric material 206 and a portion of the conductive housing 848 surrounding the opening 204, and an antenna(s) 820 positioned within the conductive housing 202 behind the dielectric material 206. In a particular embodiment, at least one dimension of the opening 204 (e.g., a length, a width, or both) is larger than a corresponding dimension of a radiating element of the antenna(s) 820.

The antenna(s) 820 may be configured to transmit and receive signals to and from one or more external devices. Lines have been drawn around the IMD 846 to illustrate various zones, including three line-of-sight zones 830, 834, and 838, and one out-of-sight zone 850. The three line-of-sight zones 830, 834, and 838 are zones in which the antenna(s) 820 is within line-of-sight through the opening 204 to the external transmitting or receiving device. Zone 830 represents signals 832 that are substantially orthogonal to the antenna(s) 820. The signal strengths of these orthogonal signals 832 should be close to maximum. Zone 834 represents signals 836 that are still in line-of-sight and slightly off of substantially orthogonal. The signal strength of these slightly off of orthogonal signals 836 should be slightly below maximum. Zone 838 represents signals 840 that are still in line-of-sight but are off of orthogonal. The signal strength of these off of orthogonal signals 840 should be lower than both the substantially orthogonal signals 832 and the slightly off of orthogonal signals 836. Zone 850 represents signals 852 that are not within line-of-sight of the antenna(s) 820. The conductive housing 802 of the case blocks the signals 852 from being received by the antenna(s) 820. The lines depicting the line-of-sight zones are provided to illustrate that there is some variation of signal strength based on the angle of the signal in relation to the antenna(s) 820 and should not be construed to be limiting. Providing the antenna(s) 820 within the conductively housing provides a more directional antenna configuration and reduces the interference seen at the antenna(s) 820 from unwanted signals.

Figure 9:
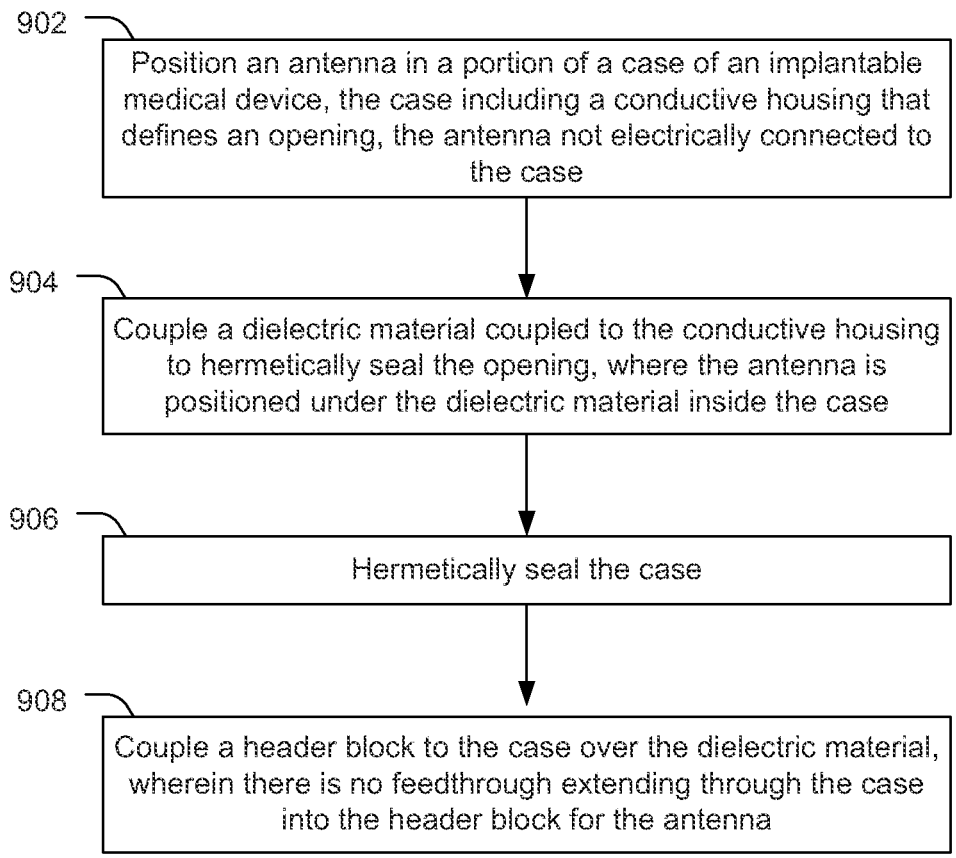
FIG. 9 is a flow chart of a method of manufacturing an implantable medical device according to a particular embodiment.

FIG. 9 is a flow chart of a method of manufacturing an implantable medical device (IMD) according to a particular embodiment. The method may be used to manufacture the IMD 100 of FIG. 1 or the IMD 200 of FIGS. 2 and 3. The method may include, at 902, positioning an antenna in a portion of a case of the IMD. The case may include a conductive housing that defines an opening. The antenna is not electrically connected to the conductive housing of the case.

The method may also include, at 904, coupling a dielectric material to the conductive housing to hermetically seal the opening and an antenna may be positioned under the dielectric material inside the case. The antenna may include the first antenna 112 of FIG. 1, which may be coupled to the communication circuitry 105. In another example, the antenna may include the second antenna 132, which may be coupled to the wake-up circuitry 134. In still another example, the antenna may include one of the antennas 208, 410 or 412 of FIG. 2, 3, or 4A-4E, which may be coupled to the communication circuitry 226 or the wake-up circuitry 406 via the flexible circuit 224.

The method may include, at 906, hermetically sealing the case. For example, the conductive housing of the case may include multiple pieces which may be coupled together to form a hermetic seal. The pieces of the conductive housing may be welded, brazed, soldered, adhered or otherwise sealed together.

The method may include, at 908, coupling a header block to the case over the dielectric material where there are no feedthroughs extending through the case into the header block for the antenna so that no portion of the antenna extends through the dielectric material into the header.

Although the description above contains many specificities, these specificities are utilized to illustrate some of the exemplary embodiments of this disclosure and should not be construed as limiting the scope of the disclosure. The scope of this disclosure should be determined by the claims, their legal equivalents and the fact that it fully encompasses other embodiments which may become apparent to those skilled in the art. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods and programs of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:
1. An implantable medical device comprising:
a case including a conductive housing and a header block, the conductive housing including an opening adjacent to the header block;
a dielectric material coupled to the conductive housing to hermetically seal the opening;
the header block coupled to the conductive housing over the dielectric material;
an antenna system comprising one or more antennas, wherein the antenna system is located within the conductive housing and under the dielectric material, wherein there is no antenna feed through extending through the conductive housing into the header block;
a communication circuitry coupled to the antenna system; and
a wake-up circuitry coupled to the antenna system, wherein the wake-up circuitry is configured to cause the communication circuitry to transition from an inactive sleep state to an awaken state upon receipt of a wake-up signal from an external device;
wherein the conductive housing substantially blocks external radio frequency signals from being received by the antenna system unless the external radio frequency signals are in line of site of the antenna system through the opening in the conductive housing.

2. The implantable medical device of claim 1, wherein the opening in the conductive housing substantially attenuates radio frequency signals below a frequency.

3. The implantable medical device of claim 2, wherein the frequency is between approximately 10 MHz and 100 MHz.

4. The implantable medical device of claim 2, wherein the frequency is determined, at least in part, by a size of the opening.

5. The implantable medical device of claim 1, wherein at least one dimension of the opening is larger than a corresponding dimension of a radiating element of the antenna.

6. The implantable medical device of claim 1, further comprising an insulating layer between the antenna and an interior of the conductive housing.

7. The implantable medical device of claim 1, wherein the antenna is not electrically connected to the conductive housing.

8. The implantable medical device of claim 1, wherein the antenna is a slot-type antenna including a conductive layer on a surface of a circuit board, the conductive layer defining a radiating slot.

9. A method comprising:
   positioning an antenna system in a portion of a case of an implantable medical device,
   the case including a conductive housing and a header block, the conductive housing including an opening adjacent to the header block, where the antenna system is not electrically connected to the conductive housing;
   positioning a communication circuitry into the case and coupling the communication circuitry to the antenna system;
   positioning a wake-up circuitry into the case and coupling the wake-up circuitry to the antenna system, the wake-up circuitry configured to cause the communication circuitry to transition from an inactive sleep state to an awaken state upon receipt of a wake-up signal from an external device;
   coupling a dielectric material to the conductive housing to hermetically seal the opening, wherein the antenna system is positioned under the dielectric material inside the conductive housing;
   hermetically sealing the conductive housing; and
   coupling the header block to the conductive housing over the dielectric material, wherein there is no antenna feed through extending through the conductive housing into the header block;
   wherein the conductive housing substantially blocks external radio frequency signals from being received by the antenna system unless the external radio frequency signals are in line of site of the antenna system through the opening in the conductive housing.

10. The method of claim 9, wherein the opening in the conductive housing substantially attenuates radio frequency signals below a frequency.

* * * * *